US010450250B2

(12) United States Patent
Bonrath et al.

(10) Patent No.: US 10,450,250 B2
(45) Date of Patent: Oct. 22, 2019

(54) PRODUCTION OF FARNESOL

(71) Applicant: DSM IP Assets B.V., Heerlen (NL)

(72) Inventors: Werner Bonrath, Kaiseraugst (CH); Raphael Beumer, Kaiseraugst (CH); Jonathan Alan Medlock, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/757,685

(22) PCT Filed: Sep. 16, 2016

(86) PCT No.: PCT/EP2016/072001
§ 371 (c)(1),
(2) Date: Mar. 6, 2018

(87) PCT Pub. No.: WO2017/046346
PCT Pub. Date: Mar. 23, 2017

(65) Prior Publication Data
US 2019/0039980 A1   Feb. 7, 2019

(30) Foreign Application Priority Data

Sep. 17, 2015 (EP) .................................. 15185585

(51) Int. Cl.
| C07C 29/141 | (2006.01) |
| C07C 29/14 | (2006.01) |
| B01J 31/02 | (2006.01) |
| B01J 31/22 | (2006.01) |
| C07C 45/51 | (2006.01) |

(52) U.S. Cl.
CPC .......... *C07C 29/141* (2013.01); *B01J 31/0275* (2013.01); *B01J 31/2295* (2013.01); *C07C 29/14* (2013.01); *C07C 45/512* (2013.01)

(58) Field of Classification Search
CPC ..... C07C 29/141; C07C 29/14; C07C 45/512; B01J 31/0275; B01J 31/2295
See application file for complete search history.

(56) References Cited

U.S. PATENT DOCUMENTS

| 3,912,656 A * | 10/1975 | Andrews ............... C07C 45/512 |
| | | 502/158 |
| 3,953,524 A * | 4/1976 | Steiner ................. B01J 23/8913 |
| | | 568/824 |
| 3,981,896 A | 9/1976 | Pauling |
| 3,994,936 A | 11/1976 | Andrews et al. |
| 6,632,954 B2 * | 10/2003 | Pfaltz ..................... C07B 53/00 |
| | | 548/103 |

FOREIGN PATENT DOCUMENTS

| DE | 2412517 | 10/1974 |
| GB | 1 358 623 | 7/1974 |

OTHER PUBLICATIONS

International Search Report for PCT/EP2016/072001, dated Nov. 18, 2016, 3 pages.

* cited by examiner

*Primary Examiner* — Rosalynd A Keys
(74) *Attorney, Agent, or Firm* — Nixon & Vanderhye P.C.

(57) ABSTRACT

The present invention relates to an improved way for the production of farnesol.

14 Claims, No Drawings

PRODUCTION OF FARNESOL

This application is the U.S. national phase of International Application No. PCT/EP2016/072001 filed Sep. 16, 2016, which designated the U.S. and claims priority to EP Patent Application No. 15185585.5 filed Sep. 17, 2015, the entire contents of each of which are hereby incorporated by reference.

The present invention relates to an improved way for the production of farnesol.

Farnesol (IUPAC name 3,7,11-trimethyldodeca-2,6,10-trien-1-ol) is the following compound of formula (I)

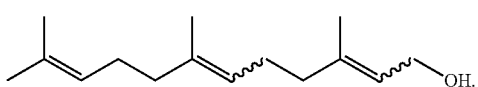
(I)

Farnesol can have several configuration isomers (E/Z), which is indicated by the wavy bonds.

There are four isomers (2E,6E)-farnesol, (2Z,6Z)-farnesol, (2E,6Z)-farnesol and (2Z,6E)-farnesol.

An important isomer of these four is for example the (2E,6E)-farnesol.

Farnesol is an important product in the cosmetic and in the perfumery industry.

In nature farnesol can be found in many essential oils such as citronella, neroli, cyclamen, lemon grass, tuberose, rose, musk, balsam and tolu.

Nowadays farnesol is produced synthetically from nerolidol (compound of formula (IV))

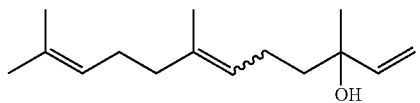
(IV)

by an acidic isomerization. The huge disadvantage is that the process (also more than 1 step) is not leading to good yields.

Due to its importance there is always a need for an improved way to produce farnesol, which does not have the disadvantages of the prior art.

A new and improved process was found wherein farnesol is produced from dehydronerolidol via farnesal. The yields in each of these reactions are always more than 80%, which results in an excellent yield of farnesol in the end. Furthermore the present process of the present invention uses mononuclear metal catalysts, which are easy to handle after the use (recycling !). Until now Pt/Co catalyst are used.

Therefore the present invention relates to a process (P) for the production of the compound of formula (I)

(I)

wherein step (1) the compound of formula (II)

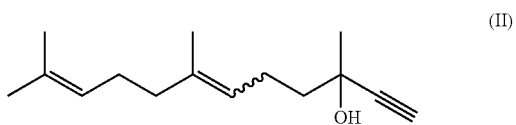 [SMILES: C#CC(C)(O)CCC=C(C)CCC=C(C)C]
(II)

is reacted to a compound (III) by a rearrangement process in the presence of at least one mononuclear metal catalyst

(III)

and wherein step (2) the compound of formula (III) is reduced to a compound of formula (I).

Step (1)

Step (1) is carried out in the presence of at least one mononuclear metal catalyst. By the term "mononuclear metal catalyst" we mean that the catalyst only comprises one specific catalytically active metal. No mixtures of catalytically active metals are used. As stated above, the use of these mononuclear metal catalyst is useful for an easy recycling of the catalyst after the reaction.

Suitable catalysts are mononuclear transition metal catalysts. Preferred mononuclear catalysts are vanadium (V)-catalysts.

More preferred are vanadium (V) catalysts of the following formula

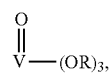

wherein
R is an alkyl or aryl group or a $M(R_1)_3$ group, wherein M is Si, Sn or Ge and $R_1$ is an alkyl or aryl group.

Especially preferred are the catalysts of the following formulae:

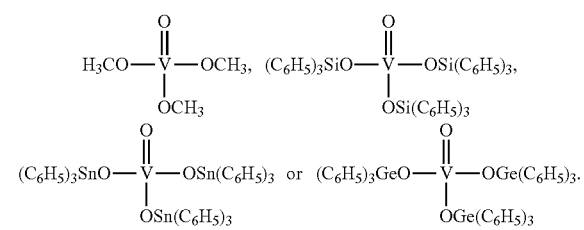

Most preferred is

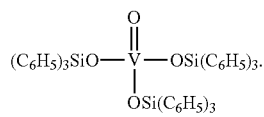

The substrate (compound of formula (II)) to catalyst ratio in the process of step (1), which is based on weight, is usually and preferably 10:1 to 500:1.

The reaction of step (1) is usually and preferably carried out in at least one solvent, which is non-polar aprotic. Preferred are aliphatic solvents having a high boiling point (above 280° C.), as well as aromatic solvents, such as xylene or toluene.

More preferred are oils having a boiling point of more than 280° C.

Therefore present invention also relates to a process (P1), which is process (P), wherein step (1) the reaction is carried out in the presence of at least one mononuclear catalyst chosen from the group consisting of

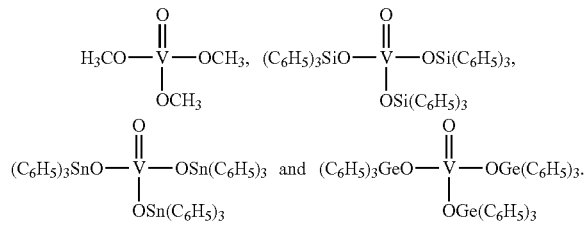

Therefore present invention also relates to a process (P1'), which is process (P1), wherein step (1) the reaction is carried out in the presence of

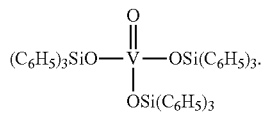

Therefore present invention also relates to a process (P1"), which is process (P1) or (P1'), wherein step (1) the substrate (compound of formula (II) to catalyst ratio, which is based on weight, is 10:1 to 500:1.

Furthermore, it was found when a small amount of at least one saturated fatty acid with a 16-22 carbon chain is added, the yield of the reaction of step (1) can be further improved.

Preferred saturated fatty acids 16-22 with a carbon chain are stearic acid, palmitic acid, arachidic acid and behenic acid, more preferred is stearic acid.

When at least one saturated fatty acid with a 16-22 carbon chain is added then in an amount of 0.001-0.015 mol equivalent (in regard to dehydronerolidol).

Therefore present invention also relates to a process (P2), which is process (P), (P1), (P1') or (P1"), wherein at least one least one saturated fatty acid with a 16-22 carbon chain is used.

Therefore present invention also relates to a process (P2'), which is process (P2), wherein at least one least one saturated fatty acid with a 16-22 carbon chain chosen from the groups consisting of stearic acid, palmitic acid, arachidic acid and behenic acid is used.

Therefore present invention also relates to a process (P2"), which is process (P2) or (P2'), wherein 0.001-0.015 mol equivalent (in regard dehydronerolidol) of least one saturated fatty acid with a 16-22 carbon chain is used.

Therefore present invention also relates to a process (P3), which is process (P), (P1), (P1'), (P1"), (P2), (P2') or (P2"), wherein step (1) the reaction is carried out in at least one solvent, which is non-polar aprotic. Preferred are aliphatic solvents having a high boiling point (above 280° C.), as well as aromatic solvents, such as xylene or toluene. More preferred are oils having a boiling point of more than 280° C.

Therefore present invention also relates to a process (P3'), which is process (P3), wherein the solvents are aliphatic solvents having a high boiling point (above 280° C.) or aromatic solvents (such as xylene or toluene).

Therefore present invention also relates to a process (P3"), which is process (P3), wherein the solvents are oils having a boiling point of more than 280° C.

The reaction of step (1) is usually and preferably carried out at an elevated temperature. The temperature depends on the solvent, which is used. Usually the temperature is between 30° C. and 180° C.

The step (1) can be carried out under pressure. When the process is carried out under pressure it is usually between 2-10 bar.

The reaction time of step (1) is not critical and therefore it can vary.

Step (2)

The reaction of step (2) is a reduction process, usually and preferably a hydrogenation, especially preferred is a transfer hydrogenation.

Therefore present invention also relates to a process (P4), which is process (P), (P1), (P1'), (P1"), (P2), (P2'), (P2"), (P3), (P3') or (P3"), wherein step (2) is a hydrogenation, preferably a transfer hydrogenation.

When the hydrogenation is carried out with $H_2$-gas, then at least one homogeneous metal catalyst can be used. Any commonly known catalyst for such a type of reaction can be used.

The metals of the homogeneous metal catalyst are chosen from the group consisting of Fe, Os, Ir, Rh and Ru, preferred is Ru. A preferred catalyst is bis phosphine Ru diamine.

Therefore present invention also relates to a process (P5), which is process (P4), wherein the hydrogenation in step (2) is carried out with Hz-gas in the presence of at least one homogeneous metal catalyst.

Therefore present invention also relates to a process (P5'), which is process (P5), wherein step (2) the metal of the homogenous metal catalyst is chosen from the group consisting of Fe, Os, Ir, Rh and Ru, preferred is Ru.

Therefore present invention also relates to a process (P5"), which is process (P5), wherein step (2) the homogenous metal catalyst is bis phosphine Ru diamine.

When the hydrogenation is carried out with Hz-gas, then it is also possible to use a heterogeneous catalysts. Any commonly known catalyst for such a type of reaction can be used. Preferred heterogeneous catalysts are those where the metal is on a support material (such as for example $CaCO_3$ or charcoal).

The metals for such a metal catalyst are chosen from the group consisting of Pt, Pd, Rh and Ru, preferred is Ru.

Therefore present invention also relates to a process (P6), which is process (P4), wherein the hydrogenation in step (2) is carried out with Hz-gas in the presence of at least one heterogeneous metal catalysts.

Therefore present invention also relates to a process (P6'), which is process (P6), wherein step (2) the metal is chosen from the group consisting of Pt, Pd, Rh and Ru and wherein the metal is on a support material (such as for example $CaCO_3$ or charcoal).

When Hz-gas is used then the applied pressure is usually between 2-20 bar.

Therefore present invention also relates to a process (P7), which is process (P5), (P5'), (P5"), (P6) or (P6'), wherein step (2) the pressure is usually between 2-20 bar.

The reaction of step (2) can also be a transfer hydrogenation. Such a transfer hydrogenation is usually and preferably carried out in the presence of a metal-complex and a hydrogen source.

Therefore present invention also relates to a process (P8), which is process (P), (P1), (P1'), (P1"), (P2), (P2'), (P2"), (P3), (P3'), (P3") or (P4), wherein step (2) the hydrogenation is a transfer hydrogenation.

Therefore present invention also relates to a process (P9), which is process (P8), wherein step (2) the transfer hydrogenation is carried out in the presence of at least one metal-complex and at least one hydrogen source.

The metal complex comprises are least one metal and at least one organic ligand. The metals of such a metal complex are chosen from the group consisting of Ir, Rh and Ru. Preferred metal complexes are pentamethylcyclopentadienyl Ir-complex (Cp*Ir), Cp*Rh, Ru-arene-complexes. Especially preferred are Ru-(p-cymene) and Ru-benzene complexes. The metal complex usually and preferably also comprises at least one organic ligand, which comprises at least one N and/or P atom. Especially preferred as a ligand are 1,2 amino alcohols and mono-sulfonated 1,2-diamines.

Therefore present invention also relates to a process (P10), which is process (P8) or (P9), wherein step (2) the transfer hydrogenation is carried out in the presence of at least one metal-complex, wherein the metal is chosen from the group consisting of Ir, Rh and Ru. Therefore present invention also relates to a process (P10'), which is process (P10), wherein the metal-complex is chosen from the group consisting of pentamethylcyclopentadienyl Ir-complex (Cp*Ir), Cp*Rh, Ru-arene-complexes, preferably Ru-(p-cymene) and Ru-benzene complexes.

Therefore present invention also relates to a process (P11), which is process (P8) (P9), (P10) or (P10'), wherein the metal-complex also comprises at least one organic ligand, which comprises at least one N and/or P atom.

Therefore present invention also relates to a process (P11'), which is process (P11), wherein the organic ligands are 1,2 amino alcohols and/or mono-sulfonated 1,2-diamines.

As stated above the transfer hydrogenation also requires a hydrogen source. Usually and preferably this can be an alcohol (or a salt thereof), formic acid (or a salt thereof) or also a formic acid/trimethylamine complex. More preferred the hydrogen source is a formic acid/triethylamine complex (5:2).

The metal complexes can be prepared in situ or added as such.

Therefore present invention also relates to a process (P12), which is process (P8), (P9), (P10), (P10'), (P11) or (P11'), wherein step (2) the transfer hydrogenation is carried out in the presence of at least one alcohol (or a salt thereof), formic acid (or a salt thereof) or a formic acid/trimethylamine complex.

Therefore present invention also relates to a process (P12'), which is process (P8), (P9), (P10), (P10'), (P11) or (P11'), wherein step (2) the transfer hydrogenation is carried out in the presence of a formic acid/triethylamine complex (5:2).

The reaction temperature of the reaction of step (2) is usually between 0-100° C., preferably between 10-70° C., more preferred between 15-30° C.

Therefore present invention also relates to a process (P13), which is process (P), (P1), (P1'), (P1"), (P2), (P2'), (P2"), (P3), (P3'), (P3"), (P4), (P5), (P5'), (P5"), (P6), (P6'), (P7), (P8), (P9), (P10), (P10'), (P11), (P11'), (P12) or (P12'), wherein step (2) the reaction temperature is usually between 0-100° C., preferably between 10-70° C., more preferred between 15-30° C.

The reaction of step (2) is usually and preferably carried out in at least one solvent.

The solvent (or mixture of solvents) is usually and preferably at least one aprotic polar solvent. Preferred solvents are esters such as ethyl acetate, iso-propyl acetate or butyl acetate.

Therefore present invention also relates to a process (P14), which is process (P), (P1), (P1'), (P1"), (P2), (P2'), (P2"), (P3), (P3'), (P3"), (P4), (P5), (P5'), (P5"), (P6), (P6'), (P7), (P8), (P9), (P10), (P10'), (P11), (P11'), (P12), (P12') or (P13) wherein step (2) is carried out in at least one solvent.

Therefore present invention also relates to a process (P14'), which is process (P14), wherein step (2), the solvent is at least one aprotic polar solvent.

Therefore present invention also relates to a process (P14"), which is process (P14), wherein step (2), the solvent is chosen from the group consisting of esters such as ethyl acetate, iso-propyl acetate and butyl acetate.

The product (compound of formula (I) is obtained in excellent yields.

The invention is illustrated by the following Examples. All percentages are related to the weight.

EXAMPLES

Example 1

E,Z-dehydronerolidol to (2E/6E, 2Z/6E, 2E/6Z, 2Z/6Z)-farnesol (step (1)) 36.6 g (0.163 Mol) of E,Z-dehydronerolidol, and 465 mg (1.63 mMol) of stearic acid, and 5.90 g (0.212 Mol) of triphenylsilanol, and 2.95 g (3.26 mMol) of tris-(triphenylsiloxy)-vanadium oxide and 163 g of vacuum pump oil were weighed into the 350 ml four-necked flask.

The reaction mixture was heated up to 140° C. under a slight argon overflow.

The reaction mixture was stirred for five hours. Afterwards the reaction mixture was cooled down to room temperature and the product ((2E/6E, 2Z/6E, 2E/6Z, 2Z/6Z)-farnesal) was obtained by distillation in a yield of 82.6%. The amount of the 4 ((2E/6E, 2Z/6E, 2E/6Z, 2Z/6Z)-farnesal isomers were (32 wt-%, 24 wt-%, 25 wt-%, 19 wt-%).

Example 2

The same reaction as in Example 1 was carried out but instead of vacuum pump oil xylenes was used as a solvent.

The yield ((2E/6E, 2Z/6E, 2E/6Z, 2Z/6Z)-farnesal was 82.2%. The amount of the 4 ((2E/6E, 2Z/6E, 2E/6Z, 2Z/6Z)-farnesal isomers were (34 wt-%, 24 wt-%, 25 wt-%, 17 wt-%)

Example 3

The same reaction as in Example 1 was carried out, but without stearic acid.

The yield ((2E/6E, 2Z/6E, 2E/6Z, 2Z/6Z)-farnesal was 79.9%. The amount of the 4 ((2E/6E, 2Z/6E, 2E/6Z, 2Z/6Z)-farnesal isomers were (29 wt-%, 19 wt-%, 31 wt-%, 21 wt-%)

Example 4

E-dehydronerolidol to (2E/6E, 2Z/6E)-farnesol

The same reaction as in Example 1 was carried out, but E-dehydronerolidol was used as starting material.

The yield (2E/6E, 2Z/6E)-farnesal was 89.2%. The amount of the 2 (2E/6E, 2Z/6E)-farnesal isomers were (52 wt-%, 48 wt-%)

Example 5

(2E/6E, 2Z/6E, 2E/6Z, 2Z/6Z)-farnesal to (2E/6E, 2Z/6E, 2E/6Z, 2Z/6Z)-farnesol (step (2))

In a 25 ml round bottomed flask with magnetic stirrer and argon overlay 12.3 mg (0.02 mMol) of dichloro(p-cymene) ruthenium(II) dimer and 9.5 mg (0.044 mMol) of N-(2-aminoethyl)-4-methylbenzenesulfonamide were solved in 9 ml (8.05 g; 91 mMol) of ethyl acetate under stirring for 30 minutes at room temperature.

Afterwards 1.74 g (20 mMol) of formic acid triethylamine complex 5:2 and then 1.07 g (4.9 mMol) of farnesal (2E/6E, 2Z/6E, 2E/6Z, 2Z/6Z)-farnesal) (obtained from example 1) were weighed in. The solution was stirred for 20 hours at RT.

(2E/6E, 2Z/6E, 2E/6Z, 2Z/6Z)-farnesol was obtained in yield of 98%. The amount of the 4 (2E/6E, 2Z/6E, 2E/6Z, 2Z/6Z)-farnesal isomers were (28 wt-%, 25 wt-%, 25 wt-%, 22 wt-%)

Example 6

(2E/6E, 2Z/6E, 2E/6Z, 2Z/6Z)-farnesal to (2E/6E, 2Z/6E, 2E/6Z, 2Z/6Z)-farnesol (step (2))

In a 250 ml flask with magnetic stirrer and argon overlay 8.75 g (32.6 mMol) of farnesal ((2E/6E, 2Z/6E, 2E/6Z, 2Z/6Z)-farnesal) (obtained by example 1) and 6.66 mg (23.6 mMol) of triisopropoxyaluminum were solved in 20.5 g (342 mMol) of isopropanol. The reaction mixture was stirred under reflux at a temperature of 98° C. for 19 h.

Afterwards (2E/6E, 2Z/6E, 2E/6Z, 2Z/6Z)-farnesol was obtained by extraction at yield of 81.4%. The amount of the 4 (2E/6E, 2Z/6E, 2E/6Z, 2Z/6Z)-farnesal isomers were (29 wt-%, 25 wt-%, 25 wt-%, 21 wt-%)

Example 7

(2E/6E, 2Z/6E)-farnesal to (2E/6E, 2Z/6E)-farnesol (step (2))

The same reaction as in Example 5 was carried out, but (2E/6E, 2Z/6E)-farnesal from Example 4 was used as starting material.

The yield (2E/6E, 2Z/6E)-farnesol was 86.2%. The amount of the 2 (2E/6E, 2Z/6E)-farnesol isomers were (52 wt-%, 48 wt-

The invention claimed is:
1. A process for the production of the compound of formula (I):

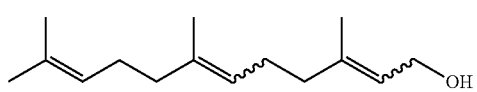

wherein the process comprises the steps of:
(1) reacting a compound of formula (II):

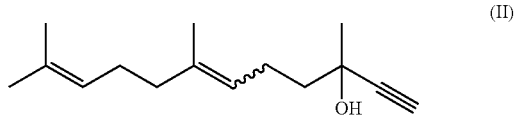 [SMILES: C#CC(C)(O)CCC=C(C)CCC=C(C)C]

by a rearrangement process in the presence of:
(i) at least one mononuclear vanadium catalyst having the following formula:

wherein R is an alkyl or aryl group or a $M(R_1)_3$ group, where M is Si, Sn or Ge and $R_1$ is an alkyl or aryl group, and wherein the catalyst is present in a weight ratio of the compound of formula (II) to the catalyst in a range of 10:1 to 500:1, and
(ii) 0.001 to 0.015 mol equivalent relative to the compound of formula (II) at least one least one saturated fatty acid with a 16-22 carbon chain selected from the group consisting of stearic acid, palmitic acid, arachidic acid and behenic acid to thereby form a compound of formula (III):

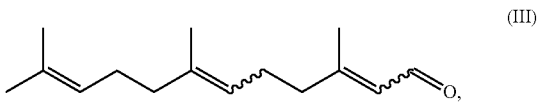 [SMILES: CC(C)=CCCC(C)=CCCC(C)=CC=O]

and thereafter
(2) conducting hydrogenation of the compound of formula (III) to the compound of formula (I).

2. The process according to claim 1, wherein the mononuclear vandium catalyst is at least one catalyst compound selected from the group consisting of:

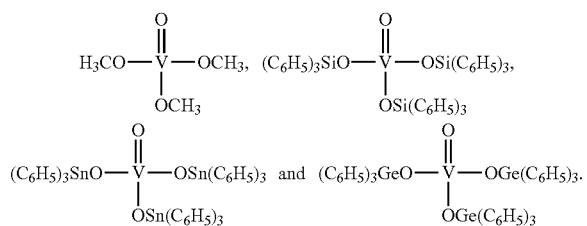

3. The process according to claim 1, wherein the reaction of step (1) is carried out in at least one non-polar aprotic solvent.

4. The process according to claim 3, wherein the at least one non-polar aprotic solvent is selected from aliphatic solvents having a boiling point above 280° C., and aromatic solvents.

5. The process according to claim 1, wherein the reaction of step (1) is carried out at a temperature between 30° C. and 180° C.

6. The process according to claim 1 wherein the hydrogenation of step (2) is carried out with $H_2$ gas.

7. The process according to claim 1, wherein the hydrogenation of step (2) is a transfer hydrogenation.

8. The process according to claim 7, wherein the transfer hydrogenation is carried out in the presence of at least one metal-complex, wherein the metal is selected from the group consisting of Ir, Rh and Ru.

9. The process according to claim 8, wherein the metal-complex is selected from the group consisting of pentamethylcyclopentadienyl Ir-complex (Cp*Ir), pentamethylcyclopentadienyl Rh-complex (Cp*Rh) and Ru-arene-complexes.

10. The process according to claim 8, wherein the metal-complex also comprises at least one organic ligand which comprises at least one N and/or P atom.

11. The process according to claim 10, wherein the at least one organic ligand comprises 1,2 amino alcohols and/or mono-sulfonated 1,2-diamines.

12. The process according to claim 7, wherein the transfer hydrogenation is carried out in the presence of at least one alcohol or a salt thereof, formic acid or a salt thereof or a formic acid/trimethylamine complex.

13. The process according to claim 4, wherein the solvent is xylene or toluene.

14. The process according to claim 9, wherein the metal-complex is a Ru-p-cymene complex or a Ru-benzene complex.

* * * * *